US010758470B2

(12) United States Patent
Pavlovic et al.

(10) Patent No.: US 10,758,470 B2
(45) Date of Patent: *Sep. 1, 2020

(54) CROSS LINKED SILK-HYALURONIC ACID COMPOSITION

(71) Applicant: Allergan, Inc., Irvine, CA (US)

(72) Inventors: Elizabeta Pavlovic, Santa Barbara, CA (US); Monica A. Serban, Melrose, MA (US); Xiaojie Yu, Irvine, CA (US); Nicholas J. Manesis, Escondido, CA (US)

(73) Assignee: ALLERGAN, INC., Irvine, CA (US)

( * ) Notice: Subject to any disclaimer, the term of this patent is extended or adjusted under 35 U.S.C. 154(b) by 8 days.

This patent is subject to a terminal disclaimer.

(21) Appl. No.: 16/024,559

(22) Filed: Jun. 29, 2018

(65) Prior Publication Data

US 2018/0303742 A1    Oct. 25, 2018

Related U.S. Application Data

(63) Continuation of application No. 15/244,587, filed on Aug. 23, 2016, now Pat. No. 10,154,951, which is a continuation of application No. 13/868,010, filed on Apr. 22, 2013, now abandoned.

(51) Int. Cl.

| *A61K 8/64* | (2006.01) |
|---|---|
| *A61Q 19/08* | (2006.01) |
| *C08B 37/08* | (2006.01) |
| *C08H 1/00* | (2006.01) |
| *C08J 3/24* | (2006.01) |
| *A61K 8/73* | (2006.01) |
| *A61L 27/20* | (2006.01) |
| *A61L 27/36* | (2006.01) |
| *A61L 27/52* | (2006.01) |
| *C08L 5/08* | (2006.01) |
| *A61L 27/22* | (2006.01) |
| *C08J 3/075* | (2006.01) |
| *C08L 89/00* | (2006.01) |

(52) U.S. Cl.

CPC ............... *A61K 8/64* (2013.01); *A61K 8/735* (2013.01); *A61L 27/20* (2013.01); *A61L 27/227* (2013.01); *A61L 27/3604* (2013.01); *A61L 27/52* (2013.01); *A61Q 19/08* (2013.01); *C08B 37/0072* (2013.01); *C08H 1/00* (2013.01); *C08J 3/075* (2013.01); *C08J 3/246* (2013.01); *C08L 5/08* (2013.01); *C08L 89/00* (2013.01); *A61L 2400/06* (2013.01); *A61L 2430/04* (2013.01); *A61L 2430/34* (2013.01); *C08J 2305/08* (2013.01); *C08J 2489/00* (2013.01); *C08J 2489/04* (2013.01)

(58) Field of Classification Search
None
See application file for complete search history.

(56) References Cited

U.S. PATENT DOCUMENTS

| 5,017,229 | A | 5/1991 | Burns et al. |
|---|---|---|---|
| 6,610,669 | B1 | 8/2003 | Calais et al. |
| 6,903,199 | B2 | 6/2005 | Moon et al. |
| 9,149,422 | B2 | 10/2015 | Liu et al. |
| 9,393,263 | B2 | 7/2016 | Liu et al. |
| 9,408,797 | B2 | 8/2016 | Njikang et al. |
| 9,737,633 | B2 | 8/2017 | Liu et al. |
| 9,950,092 | B2 | 4/2018 | Njikang et al. |
| 9,962,464 | B2 | 5/2018 | Liu et al. |
| 2001/0039336 | A1 | 11/2001 | Miller et al. |
| 2003/0096879 | A1 | 5/2003 | Fratini et al. |
| 2007/0196426 | A1 | 8/2007 | Hermitte et al. |
| 2008/0004421 | A1 | 1/2008 | Chenault et al. |
| 2009/0017091 | A1 | 1/2009 | Daniloff et al. |
| 2009/0143331 | A1 | 6/2009 | Stroumpolis et al. |
| 2009/0263447 | A1 | 10/2009 | Asius et al. |
| 2010/0016886 | A1 | 1/2010 | Lu |
| 2010/0316683 | A1 | 12/2010 | Piron et al. |
| 2011/0171286 | A1 | 7/2011 | Cecile et al. |
| 2011/0171311 | A1 | 7/2011 | Gousse et al. |
| 2012/0301436 | A1 | 11/2012 | Yang et al. |
| 2013/0096081 | A1 | 4/2013 | Njikang et al. |
| 2013/0236429 | A1 | 9/2013 | Melero-Martin |
| 2014/0315828 | A1 | 10/2014 | Pavlovic et al. |
| 2015/0064147 | A1 | 3/2015 | Pollock et al. |
| 2016/0113855 | A1 | 4/2016 | Njikang |
| 2017/0136145 | A1 | 5/2017 | Liu et al. |

FOREIGN PATENT DOCUMENTS

| CN | 102836465 | 12/2012 |
|---|---|---|
| EP | 1115433 | 12/2004 |
| EP | 1932530 | 6/2008 |
| FR | 2873379 | 1/2006 |

(Continued)

OTHER PUBLICATIONS

"BELOTERO—It's a part of me," Merz Aesthetics, retrieved from http://www.melon.fi/fi/esitteet/Belotero%20product%20catalogue.pdf.

Brandt et al., "Hyaluronic Acid Gel Fillers in the Management of Facial Aging," Clinical Interventions in Aging, 2008, 153-159, 3(1).

Database WPI, Week 201140, Thomson Scientific, London, GB, AN2011-G55502 & WO 2011/068303 A2 (Cellinbio Co Ltd) dated Jun. 9, 2011 (Jun. 9, 2011).

(Continued)

*Primary Examiner* — Jessica Worsham

(74) *Attorney, Agent, or Firm* — Nathan S. Smith; Richard W. Martin; Morgan, Lewis & Bockius LLP

(57) ABSTRACT

Compositions useful as dermal fillers and methods using such compositions to treat various skin and soft tissue conditions. The dermal fillers can comprise silk attached to hyaluronic acid using for example two cross linkers and can be used to treat of facial imperfections, facial defects, facial augmentations, breast imperfections, breast augmentations or breast reconstructions.

16 Claims, No Drawings

(56) References Cited

FOREIGN PATENT DOCUMENTS

| JP | 2009-508991 | 3/2009 |
|---|---|---|
| JP | 2009-528438 | 8/2009 |
| JP | 2010-509425 | 3/2010 |
| WO | WO 01/058961 | 8/2001 |
| WO | WO 2004/067575 | 8/2004 |
| WO | WO 2007/127277 | 12/2007 |
| WO | WO 2009/018076 | 2/2009 |
| WO | WO 2009/073437 | 6/2009 |
| WO | WO 2010/029344 | 3/2010 |
| WO | WO 2010/123945 | 10/2010 |
| WO | WO 2011/023355 | 10/2011 |
| WO | WO 2012/167079 | 12/2012 |
| WO | WO 2013/040242 | 3/2013 |
| WO | WO 2017/031169 | 2/2017 |

OTHER PUBLICATIONS

Huang et al., "New Adipose Tissue Formation by Human Adipose-Derived Stem Cells with Hyaluronic Acid Gel in Immunodeficient Mice," International Journal of Medical Sciences, Jan. 2015, vol. 12, pp. 154-162.

International Search Report and Written Opinion from PCT/2017/048495, dated Nov. 2, 2017, 9 pages.

Jeon et al., "Mechanical Properties and Degradation Behaviors of Hyaluronic Acid Hydrogels Cross-Linked at Carious Cross-Linked Densities," Carbohydrate Polymers, 2007, 251-257, 70.

Meves et al., "Vitamin C Derivative Ascorbyl Palmitate Promotes Ultraviolet-B-Induced Lipid Peroxidation and Cytotoxicity in Keratinocytes," The Journal of Investigative Dermatology, Nov. 2002, 1103-1108, vol. 119, No. 5.

Murphy et al., "Biomedical applications of chemically-modified silk fibroin," Journal of Materials Chemistry, 2009, 19, 6443-6450.

Park et al., "In Vitro Evaluation of Conjugated Hyaluronic Acid With Ascorbic Acid," Journal of Bone and Joint Surgery, 2010, 115 92.

Tomihata et al., "Crosslinking of Hyaluronic Acid with Water-Soluable Carbodiimide," J Biomed Mater Res, Feb. 1997, 243-251, vol. 37(2).

Yeom et al., "Effect of Cross-Linking Reagents for Hyaluronic Acid Hydrogel Dermal Fillers on Tissue Augmentation and Regeneration," Bioconjugate Chem, 2010.

Zhu et al., "Manual Isolation of Adipose-derived Stem Cells from Human Lipoaspirates," J. Vis. Exp. (79) e50585, Sep. 2013, 10 pages.

CROSS LINKED SILK-HYALURONIC ACID COMPOSITION

CROSS-REFERENCE TO RELATED APPLICATIONS

This application is a continuation of U.S. patent application Ser. No. 15/244,587, filed Aug. 23, 2016, which is a continuation of U.S. patent application Ser. No. 13/868,010, filed Apr. 22, 2013, the entire disclosure of each of these applications is incorporated herein by this specific reference.

BACKGROUND

The present invention relates to a cross linked silk-hyaluronic acid composition, methods of making and uses thereof. In particular the present invention relates a cross linked silk fibroin-polymeric hyaluronic acid composition useful for example as a dermal filler or to facilitate adipose tissue transfer and grafting procedures.

Hyaluronic acid (HA) (synonymously "hyaluron" or "hyaluronate") is a naturally occurring glucosaminoglycan that has been used as a constituent of a dermal filler for wrinkle reduction and tissue volumizing. Hyaluronan is an anionic, nonsulfated glycosaminoglycan distributed widely throughout connective, epithelial, and neural tissues. Polymeric hyaluronic acid can have a molecular weight of several million Daltons. A person typically has about 15 grams of hyaluronan in his body about a third of which every day is degraded by endogenous enzymes and free radicals within a few hours or days and replaced by hyaluronic acid newly synthesized by the body.

Silk is a natural (non-synthetic) protein made of high strength fibroin fibers with mechanical properties similar to or better than many of synthetic high performance fibers. Silk is also stable at physiological temperatures in a wide range of pH, and is insoluble in most aqueous and organic solvents. As a protein, unlike the case with most if not all synthetic polymers, the degradation products (e.g. peptides, amino acids) of silk are biocompatible. Silk is non-mammalian derived and carries far less bioburden than other comparable natural biomaterials (e.g. bovine or porcine derived collagen). Silk, as the term is generally known in the art, means a filamentous fiber product secreted by an organism such as a silkworm or spider. Silks can be made by certain insects such as for example *Bombyx mori* silkworms, and *Nephila clavipes* spiders. There are many variants of natural silk. Fibroin is produced and secreted by a silkworm's two silk glands. As fibroin leaves the glands it is coated with sericin a glue-like substance. Spider silk is produced as a single filament lacking the immunogenic protein sericin.

Silk has been used in biomedical applications. The Bombyx mori species of silkworm produces a silk fiber (a "bave") and uses the fiber to build its cocoon. The bave as produced include two fibroin filaments or broins which are surrounded with a coating of the gummy, antigenic protein sericin. Silk fibers harvested for making textiles, sutures and clothing are not sericin extracted or are sericin depleted or only to a minor extent and typically the silk remains at least 10% to 26% by weight sericin. Retaining the sericin coating protects the frail fibroin filaments from fraying during textile manufacture. Hence textile grade silk is generally made of sericin coated silk fibroin fibers. Medical grade silkworm silk is used as either as virgin silk suture, where the sericin has not been removed, or as a silk suture from which the sericin has been removed and replaced with a wax or silicone coating to provide a barrier between the silk fibroin and the body tissue and cells. Thus there is a need for a sericin extracted implantable, bioresorbable silk device that promotes ingrowth of cells.

Bioconjugate Chemistry, 2010, 21, 240-247: Joem Y., et al., *Effect of cross-linking reagents for hyaluronic acid hydrogel dermal fillers on tissue augmentation and regeneration,* discusses use of a particular cross-linked HMDA to prepare a cross-linked hyaluronic acid dermal filler, and also discloses use of a variety of hyaluronic acid cross linkers and hyaluronic activators including BDDE and EDC. Carbohydrate Polymers, 2007, 70, 251-257: Jeon, O., et al., *Mechanical properties and degradation behaviors of hyaluronic acid hydrogels cross-linked at various cross-linking densities,* discusses properties of hyaluronic acid cross linked with a polyethylene glycol diamine (a PEG-diamine). J. Am. Chem. Soc., 1955, 77 (14), 3908-3913: Schroeder W., et al., *The amino acid composition of Bombyx mori silk fibroin and of Tussah silk fibroin,* compares the amino acid compositions of the silk from two silkworm species. US Patent Application Publication. Pub. No. US 2010/0016886 A1: Lu, H., *High swell, long lived hydrogel sealant;* discusses reacting a multi-arm amine (i.e. an 9 arm polyethelene glycol (PEG) with an oxidized (i.e. to introduce aldehyde groups) polysaccharide (such as hyaluronic acid), useful for tissue augmentation or a tissue adhesive/sealant. U.S. Pat. No. 6,903,199 to Moon. T., et al., *Cross-linked amide derivatives of hyaluronic acid and manufacturing method thereof* discusses cross linking hyaluronic acid with a chitosan or with a deacetylated hyaluronic acid with reactive amide groups, using (for example) EDC or NHS.

International Patent Application WO/2010/123945, Altman, G., et al., *Silk fibroin hydrogels and uses thereof* discusses silk hydrogels made by, for example, digesting degummed silk hydrogels made by, for example, digesting degummed *Bombyx mori* silk at 60° C. for 4 hours in 9.3M lithium bromide to thereby obtain a 20% silk solution, an 8% silk solution of which was induced to gel using 23RGD and/or ethanol, which can be present in a hyaluronic acid carrier. Altman also discusses possible use as a dermal filler and to promote wound closure, and a silk hydrogel coating on a silk mesh.

International Patent Application. Pub. No. WO/2008/008857: Prestwich, G., et al., *Tholated macromolecules and methods for making and using thereof* discloses a thioethyl ether substituted hyaluronic acid made by oxidating coupling useful, for example, in arthritis treatment. International Patent Application. Pub. No. WO/2008/008859: Prestwich, G., et al., *Macromolecules modified with electrophilic groups and methods of making and using thereof* discloses a haloacetate derivative hyaluronic acid reacted with thiol modified hyaluronic acid to make a hydrogel, with various medical uses. Biomacromolecules, 2010, 11 (9), 2230-2237: Serban, M., et. Al., *Modular elastic patches: mechanical and biological effects* discusses how to make an elastic patch by cross linking elastin, hyaluronic acid and silk, by adding an aminated hyaluronic acid (made using EDC) with a 20% silk solution and elastin, in PBS with BS3 (bissulfosuccinimidyl suberate, as cross linker) at 37° C. for 12 hours. Biomaterials, 2008, 29(10), 1388-1399: Serban, M., et al., *Synthesis, characterization and chondroprotective properties of a hyaluronan thioethyl ether derivative* discusses a viscous 2-thioethyl ether hyaluronic acid derivative solution useful for viscosupplementation in arthritis treatment. The abstract mentions that a prior hyaluronic acid with multiple thio groups can be used for adhesion prevention. Methods, 2008, 45, 93-98: Serban, M., et al., *Modular extracellular matrices: solutions to the puzzle* discusses cross linked thio modified hyaluronic acid hydrogel useful as a semi synthetic extracellular matrix for cell culture. Biomacromolecules, 2007, 8(9), 2821-2828: Serban, M., et al., *Synthesis of hyaluronan haloacetates and biology of novel cross linker free synthetic extracellular matrix hydrogels* discusses cross linking haloacetate substituted hyaluronic acids reacted with a thiol substituted hyaluronic acid to make a hydrogel useful for cell culture or adhesion prevention or medical device coating. Journal of Materials Chemistry, 2009, 19, 6443-6450: Murphy A., et al., *Biomedical applications of chemically modified silk fibroin* is a review of methods to make silk conjugates, including silk conjugated to oligosaccharides, modified silk and medical uses. Biomacromolecules, 2004, 5, 751-757: Sohn, S., et al., *Phase behavior and hydration of silk fibroin* discusses a study of *Bombyx mori* silk in vitro using osmotic stress, determining that silk I (α-silk) but not silk II (β-sheet, spun silk fiber) is hydrated. U.S. Pat. No. 8,071,722 to Kaplan, D., et al., *Silk Biomaterials and methods of use thereof* discloses silk films, use of 9-12 m LiBr to dissolve extracted silk, adding hyaluronic acid to a silk solution to make fibers from the composition. See also eg the Kaplan patents and application U.S. Pat. Nos. 7,674,882; 8,178,656; 2010 055438, and; 2011 223153. US patent application 2011 071239 by Kaplan, D., et al., *PH induced silk gels and uses thereof* discloses methods for making silk fibroin gel from silk fibroin solution, useful to coat a medical device using implants, as an injectable gel to fill a tissue void, making an adhesive silk gel (with or without a hyaluronic acid), adhering the adhesive silk gel to a subject for example for use as a wound bioadhesive, a multi-layered silk gel. US patent application 2009 0202614 by Kaplan, D., et al., *Methods for stepwise deposition of silk fibroin coatings* discusses layered silk coatings, silk films made using silk fibroin solutions which can include a hyaluronic acid, useful, for example, as wound healing patches, to coat an implantable medical device. U.S. Pat. No. 4,818,291 to Iwatsuki M., et al., *Silk-fibroin and human-fibrinogen adhesive composition* discusses surgical adhesive useful in tissue repair made as a mixture of LiBr dissolved silk and fibrinogen.

To increase in vivo residence time, the linear chains of hyaluronic acid can be crosslinked with a small molecular cross linker such as, for example, butanediol diglycidyl ether (BDDE) or 1-ethyl-3-[3-dimethylaminopropyl]carbodiimide hydrochloride (EDC) chemistry. Crosslinking hyaluronic acid with BDDE is usually carried out at high pH (>12) and at temperatures of about 50° C. It has been reported that the degradation rate constant of HA is increased roughly 100 times when the temperature and pH are both increased from 40 to 60° C. and 7 to 11 respectively. Hence, there is a need for cross linkers and cross linking chemistries for hyaluronic acid that can be used to cross link hyaluronic acid under milder conditions. Additionally, there is a need for a composition comprising silk attached to hyaluronic acid with medical and cosmetic uses.

SUMMARY

The present invention meets these needs and provides a composition comprising silk attached to hyaluronic acid, with medical and cosmetic uses. For example the present invention can cross link hyaluronic acid under mild conditions, for example using as the cross linking 1-ethyl-3-[3-dimethylaminopropyl]carbodiimide hydrochloride (EDC).

Hyaluronic acid gels with additives present molecular behaviors that can be used to govern bulk material properties such as mechanical and rheological parameters, chemical stability, cyto- and biocompatibility and biological activity not found in pure hyaluronic acid gels; hence, they can be used for different applications compared to the pure hyaluronic acid gels. We have invented hyaluronic acid gels wherein the hyaluronic acid is cross linked to a water-soluble silk fibroin. To obtain a solution of water-soluble silk fibroin, silk from Bombyx Mori cocoons the sericin naturally present on the silkworm silk can be removed by soaking the silk in a warm basic solution and the sericin extracted silk can then manufactured into yarn. Subsequently, the yarn can be digested (dissolved) in 9.3M LiBr and dialyzed, resulting in a MilliQ water solution of water-soluble SF in a denaturated state. The amino acid composition of *Bombyx Mori* silk fibroin shows a low amount of aspartic acid/glutamic acid (carboxylic groups), even lower amount of lysine (amine groups) and a high amount of serine (hydroxyl groups). Although BDDE can be used, EDC chemistry is used preferentially to crosslink the gels because of the mild reaction conditions. The lysine content of silk fibroin being low, the diamine cross linkers HMDA or lysine methyl ester are also used to allow for stable amide bonds to be formed between molecules. Additionally, silk beta-sheet formation could potentially be induced with accelerants (pH, temperature, vortexing, sonication, ethanol treatment, etc).

The mixing set-up used for mixing hyaluronic acid and silk fibroin influences the dispersion of silk fibroin inside the hyaluronic acid bulk. Fast mixing creating a turbulent flow, such as syringe-to-syringe passing, favors the aggregation of silk fibroin molecules and the formation of larger particles (10-70 uM) inside the gel. Using a slow laminar flow, typically in a static mixer, a uniform dispersion of silk fibroin with fewer particles (1-10 uM) is obtained. In general, the presence of silk fibroin cross linked in the hyaluronic acid gel modifies the rheological properties of the gels by increasing the hydrophobicity and the G'. This is the result of the refolding of silk fibroin into beta sheets that interact with each other when buffer salts are added, forming strong connections between silk fibroin molecules and resulting in a network-like structure which adds to the effect of the cross linking. Since the silk fibroin molecules form strong interactions between beta sheets that are not destroyed by heat, hyaluronic acid cross linked with silk fibroin gels can be sterilized by autoclaving. The G' decrease observed after autoclaving is only 5-20% of the original G' value, as opposed to up to 60% for pure HA.

Because silk fibroin contains only a small amount of COOH groups in the form of aspartic and glutamic acid residues, the hyaluronic acid-silk fibroin cross linking can be enhanced chemically or enzymatically. Hyaluronic acid can be conjugated by using either the COOH functionality of the glucuronic acid residues or the (CH2)-OH groups of the N-acetyl glucosamine residues in hyaluronic acid. Silk fibroin would be functionalized first by diazo chemistry at the tyrosine residues to introduce additional COOH functionalities. Adhesion motifs (in the form of RGD or peptides, gelatin, collagen or collagen fragments) can also be chemically attached to either hyaluronic acid or silk fibroin. Additional to the aforementioned silk fibroin amino acids suitable for chemical modifications, there are a significant number of serine residues that can be chemically modified (i.e. reaction with chloroacetic acid to introduce COOH functionalities). In one concept, an adhesion motif can be chemically grafted to either silk fibroin or hyaluronic acid, then a different functionality or a second conjugation step can be used to covalently attach silk fibroin to hyaluronic acid.

The present invention provides a composition and methods of treating a skin condition in an individual in need thereof, the method comprising the steps of administering a composition disclosed herein into a dermal region of the individual, wherein the administration improves the skin condition. Skin conditions treated by the disclosed compositions include, without limitation, augmentations, reconstructions, diseases, disorders, defects, or imperfections of a body part, region or area. In one aspect, a skin condition treated by the disclosed compositions include, without limitation, a facial augmentation, a facial reconstruction, a facial disease, a facial disorder, a facial defect, or a facial imperfection. In one aspect, a skin condition treated by the disclosed compositions include, without limitation, skin dehydration, a lack of skin elasticity, skin roughness, a lack of skin tautness, a skin stretch line or mark, skin paleness, a dermal divot, a sunken check, a thin lip, a retro-orbital defect, a facial fold, or a wrinkle.

DESCRIPTION

The present invention is based on the discovery of particular methods to cross link silk to a hyaluronic acid and uses for such a composition (the "composition"). For example the composition can be used as a dermal filler and also in conjunction with breast augmentation and reconstruction where soft tissue volumizing and/or tissue regeneration or tissue ingrowth is desired. Additionally, the composition can be used to assist the filling (i.e. volumizing) any tissue void either natural or caused by a surgical procedure that removed tissue, by a corticosteroid treatment, by an immunologic reaction resulting in lipoatrophy, tissue damage resulting from impact injuries, or due to radiological or chemical drug treatment. Similarly, the composition can be used as a means for reducing scar tissue as a result of the active vascularization and dissolution of scar tissue either as a preventative or post treatment procedure based on the delivery of viable fat-derived cells or stem or progenitor cells to the site.

In one embodiment, the composition can comprise a cellular component such as living or viable cellular components, and a filler component effectively providing volume and support for viability and growth of the cells and/or other tissue when the composition is injected into a target region of a patient.

The composition, when injected into a target region of a patient can provide relatively long term, for example, greater than six months or more, of increased tissue filling and volumizing, relative to a substantially identical composition which does not include a cellular component. The composition can also provides the support, structure and space within the tissue to allow for growth and regeneration of tissue. The cellular component in the composition can provide for the production or stimulation of cytokines and intrinsic stimulators of tissue growth and maintenance at the site of injection.

The cellular component of the present composition preferably comprises adipose-derived progenitor cells, for example, adipose-derived stem cells. In some embodiments of the invention, methods are provided for filling and regenerating tissue using such cell and filler compositions which include autologous cells, for example, autologous, adipose-derived adult stem and/or progenitor cells. The cellular component of the composition can provide relatively long-term tissue regeneration when combined with a filler component after the composition has been injected or implanted into a patient.

The filler component of the present compositions generally comprises a biocompatible material that can provide substantially immediate or short term tissue filling, and preferably, an environment conducive to cell or tissue growth.

In some embodiments, the filler component is a material that absorbs water and expands once injected into the body, to provide space for cell growth to enhance tissue regeneration. The filler component may be a material selected from the group consisting of hyaluronic acid (HA), collagen, cross linked hyaluronic acid/collagen, hydrogels and combinations thereof.

In one aspect of the invention, the filler component may further include one or more additional materials or agents which are components of a natural extracellular matrix or peptides, derivatives or analogs of integrin binding molecules, that are capable of optimizing implanted cell viability and/or sustaining cell growth for a relatively long term or sustained period of time after the injection or implantation of the composition.

The filler component may comprise, for example, a hydrogel material combined with one or more other beneficial materials, for example, integrin binding molecules, integrin binding derivatives or analogs thereof, or peptides or peptide analogs with the potential to bind to integrins on the injected cell population. Such materials may be selected based on their ability to bind to growth factor receptors to thereby stimulate cell growth, for example, the injected adipose cells and/or the influx of intrinsic tissue progenitors or cytokines.

Crosslinking HA via EDC chemistry involves the use of small multi amine cross linkers, which form amide bonds with the carboxylic functional groups of HA chains. In ideal condition, EDC activates the carboxylic acid groups of HA, and the activated carboxylic acid groups then react with the amines. Crosslinking is usually done at pH between 4-7 and temperatures between 20 and 37° C., conditions at which degradation of HA is minimal. Linear diamine cross linkers like hexamethylene diamine (NMDA), lysine, lysine methyl ester or lysine ethyl ester, have been used to crosslink HA for various applications. Protein additives with high lysine content such as Collagen can also be used. Crosslinking HA via EDC chemistry without the use of a multiamine cross linker results in the formation of ester bonds between carboxylic acid groups and the hydroxyl groups of HA. Ester bonds are very labile, and are easily hydrolyzed at high temperatures. HA hydrogels made by ester cross linking are generally not robust and cannot be sterilized with moist steam.

The present invention includes a composition comprising a gel phase including a hydrogel comprising a silk fibroin covalently attached to an HA ("the composition").

The silk fibroin used for preparing the composition is an intermediate in the silk hydrogel production process and a direct precursor to the hydrogel material. The depolymerized silk fibroin can be made from raw cocoons, previously degummed silk or any other partially cleaned silk. This may also include material commonly termed as "waste" from the reeling process, i.e. short fragments of raw or degummed silk, the sole precaution being that the silk must be substantially cleaned of sericin prior to making fibroin solution and inducing gel formation. A particular source of raw silk is from common domesticated silkworm *B. mori,* though several other sources of silk may be appropriate. This includes other strains of Bombycidae including *Antheraea pernyi, Antheraea yamamai, Antheraea mylitta, Antheraea assama,* and *Philosamia cynthia ricini,* as well as silk producing members of the families Saturnidae, Thaumetopoeidae, and silk-producing members of the order Araneae. The material may also be obtained from other spider, caterpillar, or recombinant sources.

A hydrogel disclosed herein provide for a depolymerized silk fibroin and/or silk fibroin that are substantially free of sericin. Methods for performing sericin extraction have been described in pending U.S. patent application Ser. No. 10/008,924, U.S. Publication No. 2003/0100108, Matrix for the production of tissue engineered ligaments, tendons and other tissue. That application refers to cleaned fibroin fibers spun into yarns, used to create a porous, elastic matrix suitable as a substrate for applications requiring very high tensile strength, such as bioengineered ligaments and tendons.

Extractants such as urea solution, hot water, enzyme solutions including papain among others which are known in the art to remove sericin from fibroin would also be acceptable for generation of the silk. Mechanical methods may also be used for the removal of sericin from silk fibroin. This includes but is not limited to ultrasound, abrasive scrubbing and fluid flow. The rinse post-extraction is conducted preferably with vigorous agitation to remove substantially any ionic contaminants, soluble, and in soluble debris present on the silk as monitored through microscopy and solution electrochemical measurements. A criterion is that the extractant predictably and repeatably remove the sericin coat of the source silk without significantly compromising the molecular structure of the fibroin. For example, an extraction may be evaluated for sericin removal via mass loss, amino acid content analysis, and scanning electron microscopy. Fibroin degradation may in turn be monitored by FTIR analysis, standard protein gel electrophoresis and scanning electron microscopy.

In certain cases, the silk utilized for making the composition has been substantially depleted of its native sericin content (i.e., ≤4% (w/w) residual sericin in the final extracted silk). Alternatively, higher concentrations of residual sericin may be left on the silk following extraction or the extraction step may be omitted. In preferred aspects of this embodiment, the sericin-depleted silk fibroin has, e.g. about 0% to about 4% (w/w) residual sericin. In the most preferred aspects of this embodiment, the sericin-depleted silk fibroin has, e.g. about 1% to 3% (w/w) residual sericin.

In certain cases, the silk utilized for generation of a silk hydrogel is entirely free of its native sericin content. As used herein, the term "entirely free (i.e. "consisting of" terminology) means that within the detection range of the instrument or process being used, the substance cannot be detected or its presence cannot be confirmed.

The water soluble or y dissolved silk can be prepared by a 4 hour digestion at 60° C. of pure silk fibroin at a concentration of 200 g/L in a 9.3 M aqueous solution of lithium bromide to a silk concentration of 20% (w/v). This process may be conducted by other means provided that they deliver a similar degree of dissociation to that provided by a 4 hour digestion at 60° C. of pure silk fibroin at a concentration of 200 g/L in a 9.3 M aqueous solution of lithium bromide. The primary goal of this is to create uniformly and repeatably dissociated silk fibroin molecules to ensure similar fibroin solution properties and, subsequently, device properties. Less substantially dissociated silk solution may have altered gelation kinetics resulting in differing final gel properties. The degree of dissociation may be indicated by Fourier-transform Infrared Spectroscopy (FTIR) or x-ray diffraction (XRD) and other modalities that quantitatively and qualitatively measure protein structure. Additionally, one may confirm that heavy and light chain domains of the silk fibroin dimer have remained intact following silk processing and dissolution. This may be achieved by methods such as standard protein sodium-dodecyl-sulfate polyacrylamide gel electrophoresis (SDS-PAGE) which assess molecular weight of the independent silk fibroin domains.

System parameters which may be modified in the initial dissolution of silk include but are not limited to solvent type, silk concentration, temperature, pressure, and addition of mechanical disruptive forces. Solvent types other than aqueous lithium bromide may include but are not limited to aqueous solutions, alcohol solutions, 1,1,1,3,3,3-hexafluoro-2-propanol, and hexafluoroacetone, 1-butyl-3-methylimidazolium. These solvents may be further enhanced by addition of urea or ionic species including lithium bromide, calcium chloride, lithium thiocyanate, zinc chloride, magnesium salts, sodium thiocyanate, and other lithium and calcium halides would be useful for such an application. These solvents may also be modified through adjustment of pH either by addition of acidic of basic compounds.

Cross-linking can also be accomplished without exogenous cross-linkers by utilizing reactive groups on the molecules being conjugated. Methods for chemically cross-linking peptide molecules are generally known in the art, and a number of hetero- and homobifunctional agents are described in, e.g., U.S. Pat. Nos. 4,355,023, 4,657,853, 4,676,980, 4,925,921, and 4,970,156, and Immuno Technology Catalogue and Handbook, Pierce Chemical Co. (1989), each of which is incorporated herein by reference. Such conjugation, including cross-linking, should be performed so as not to substantially affect the desired function of the peptide oligomer or entity conjugated thereto, including therapeutic agents, and moieties capable of binding substances of interest.

It will be apparent to one skilled in the art that alternative linkers can be used to link peptides, for example the use of chemical protein crosslinkers. For example homobifunctional crosslinker such as disuccinimidyl-suberimidate-dihydrochloride; dimethyl-adipimidate-dihydrochloride; 1,5,-2,4dinitrobenezene or heterobifunctional crosslinkers such as N-hydroxysuccinimidyl 2,3-dibromopropionate; lethyl-3-[3-dimethylaminopropyl] carbodiimide hydrochloride; and succinimidyl4- [n-maleimidomethyl]-cyclohexane-1-carboxylate.

A composition disclosed herein is typically a biodegradable, bioerodible, and/or bioresorbable. In an embodiment, a silk fibroin cross linked to a hyaluronic acid hydrogel disclosed herein has a protein structure that makes the hydrogel resist biodegradation, bioerosion, and/or bioresorption. In aspects of this embodiment, a hydrogel is resistant to biodegradation, bioerosion, and/or bioresorption for, e.g., between about 10 days to about 180 days. In a preferred aspect of this embodiment, a hydrogel is resistant to biodegradation, bioerosion, and/or bioresorption for, e.g., about 30 day to about 90 days. In the most preferred aspect of this embodiment, a hydrogel is resistant to biodegradation, bioerosion, and/or bioresorption for, e.g. about 20 days to 90 days.

In yet another embodiment, a silk fibroin hydrogel disclosed herein has a protein structure that substantially includes β-turn and β-strand regions. In another aspect of this embodiment, a hydrogel has a protein structure including, e.g., between about 10% to about 100% β-turn and β-strand regions. In a preferred aspect of this embodiment, a hydrogel has a protein structure including, e.g., between about 20% to about 70% β-turn and β-strand regions. In the most preferred aspect of this embodiment, a hydrogel has a protein structure including, e.g., between about 30% to about 50% β-turn and β-strand regions.

In yet another embodiment, a silk fibroin hydrogel disclosed herein has a protein structure that is substantially-free of α-helix and random coil regions. In aspects of this embodiment, a hydrogel has a protein structure including, e.g., between about 5% to about 50% α-helix and random coil regions. In some preferred aspects of this embodiment, a hydrogel has a protein structure including, e.g., between about 10% to about 40% α-helix and random coil regions. In the most preferred aspects of this embodiment, a hydrogel has a protein structure including, e.g., between about 15% to about 35% α-helix and random coil regions.

Aspects of the present specification provide, in part, a silk fibroin hydrogel having hardness. Hardness refers to various properties of an object in the solid phase that gives it high resistance to various kinds of shape change when force is applied. Hardness is measured using a durometer and is a unitless value that ranges from zero to 100. The ability or inability of a hydrogel to be easily compressed will affect its suitability for application in different tissue replacement roles, i.e., mechanical compliance as bone, fat, connective tissue. Hardness will also affect the ability of a hydrogel to be effectively comminuted, the reason being that a hard material may be more easily and consistently comminuted. Hardness will also affect extrudability, as a soft material may be more readily able to be slightly compressed during injection to pack with other particles or change shape to pass through a syringe barrel or needle.

In an embodiment, a silk fibroin hydrogel exhibits low hardness. In aspects of this embodiment, a silk fibroin hydrogel exhibits a hardness of, e.g., between about 5 to about 40. In some preferred aspects of this embodiment, a silk fibroin hydrogel exhibits a hardness of, e.g., between about 10 to about 30. In the most preferred aspects of this embodiment, a silk fibroin hydrogel exhibits a hardness of, e.g., between about 15 to about 35.

In an embodiment, a silk fibroin hydrogel exhibits medium hardness. In aspects of this embodiment, a silk fibroin hydrogel exhibits a hardness of, e.g., about 40 to about 65. In some preferred aspects of this embodiment, a silk fibroin hydrogel exhibits a hardness of, e.g., about 30 to about 55. In the most preferred aspects of this embodiment, a silk fibroin hydrogel exhibits a hardness of, e.g., about 45 to about 60.

In another embodiment, a silk fibroin hydrogel exhibits high hardness. In aspects of this embodiment, a silk hydrogel exhibits a hardness of, e.g., between about 65 to about 95. In some preferred aspects of this embodiment, a silk hydrogel exhibits a hardness of, e.g., between about 70 to about 90. In the most preferred aspects of this embodiment, a silk hydrogel exhibits a hardness of, e.g., between about 75 to about 85.

In an embodiment, a silk fibroin hydrogel exhibits high resistant to deformation. In aspects of this embodiment, a silk fibroin hydrogel exhibits resistant to deformation of, e.g., about 100% to about 85%. In some preferred aspects of this embodiment, a silk fibroin hydrogel exhibits resistant to deformation of, e.g., about 95% to about 80%. In the most preferred aspects of this embodiment, a silk fibroin hydrogel exhibits resistant to deformation of, e.g., about 93% to about 78%.

A silk fibroin hydrogel exhibits an elastic modulus. Elastic modulus, or modulus of elasticity, refers to the ability of a hydrogel material to resists deformation, or, conversely, an object's tendency to be non-permanently deformed when a force is applied to it. The elastic modulus of an object is defined as the slope of its stress-strain curve in the elastic deformation region: $\lambda$=stress/strain, where $\lambda$ is the elastic modulus in Pascal's; stress is the force causing the deformation divided by the area to which the force is applied; and strain is the ratio of the change caused by the stress to the original state of the object. Specifying how stresses are to be measured, including directions, allows for many types of elastic moduli to be defined. The three primary elastic moduli are tensile modulus, shear modulus, and bulk modulus.

Tensile modulus (E) or Young's modulus is an objects response to linear strain, or the tendency of an object to deform along an axis when opposing forces are applied along that axis. It is defined as the ratio of tensile stress to tensile strain. It is often referred to simply as the elastic modulus. The shear modulus or modulus of rigidity refers to an object's tendency to shear (the deformation of shape at constant volume) when acted upon by opposing forces. It is defined as shear stress over shear strain. The shear modulus is part of the derivation of viscosity. The shear modulus is concerned with the deformation of a solid when it experiences a force parallel to one of its surfaces while its opposite face experiences an opposing force (such as friction). The bulk modulus (K) describes volumetric elasticity or an object's resistance to uniform compression, and is the tendency of an object to deform in all directions when uniformly loaded in all directions. It is defined as volumetric stress over volumetric strain, and is the inverse of compressibility. The bulk modulus is an extension of Young's modulus to three dimensions.

In another embodiment, a silk fibroin hydrogel exhibits a tensile and/or shear modulus. In aspects of this embodiment, a silk fibroin hydrogel exhibits a tensile modulus of, e.g., about 1 MPa to about 30 GPa. In some preferred aspects of this embodiment, a silk fibroin hydrogel exhibits a tensile modulus of, e.g., about 5 MPa to about 25 GPa. In the most preferred aspects of, e.g., this embodiment, a silk fibroin hydrogel exhibits a tensile modulus of about 20 MPa to about 15 GPa.

In another embodiment, a silk fibroin hydrogel exhibits a bulk modulus. In aspects of this embodiment, a silk fibroin hydrogel exhibits a bulk modulus of, e.g., about 5 GPa to about 100 GPa. In some preferred aspects of this embodiment, a silk fibroin hydrogel exhibits a bulk modulus of, e.g., about 10 GPa to about 90 GPa. In the most preferred aspects of this embodiment, a silk fibroin hydrogel exhibits a bulk modulus of, e.g., about 25 GPa to about 85 GPa.

A silk fibroin hydrogel exhibits high tensile strength. Tensile strength has three different definitional points of stress maxima. Yield strength refers to the stress at which material strain changes from elastic deformation to plastic deformation, causing it to deform permanently. Ultimate strength refers to the maximum stress a material can withstand when subjected to tension, compression or shearing. It is the maximum stress on the stress-strain curve. Breaking strength refers to the stress coordinate on the stress-strain curve at the point of rupture, or when the material pulls apart.

In another embodiment, a silk fibroin hydrogel exhibits high yield, high ultimate, and/or high breaking strength relative to other polymer classes. In aspects of this embodiment, a silk fibroin hydrogel exhibits a yield strength of, e.g., about 0.1 MPa to about 500 MPa. In some preferred aspects of this embodiment, a silk fibroin hydrogel exhibits a yield strength of, e.g., about 5 MPa to about 400 MPa. In the most preferred aspects of this embodiment, a silk fibroin hydrogel exhibits a yield strength of e.g., about 20 MPa to about 300 MPa.

Aspects of the present specification provide, in part, a silk fibroin hydrogel having a transparency and/or translucency. Transparency (also called pellucidity or diaphaneity) is the physical property of allowing light to pass through a material, whereas translucency (also called translucence or translucidity) only allows light to pass through diffusely. The opposite property is opacity. Transparent materials are clear, while translucent ones cannot be seen through clearly. The silk fibroin hydrogels disclosed herein may, or may not, exhibit optical properties such as transparency and translucency. In certain cases, e.g., superficial line filling, it would be an advantage to have an opaque hydrogel. In other cases such as development of a lens or a "humor" for filling the eye, it would be an advantage to have a translucent hydrogel. These properties could be modified by affecting the structural distribution of the hydrogel material. Factors used to control a hydrogel's optical properties include, without limitation, silk fibroin concentration, gel crystallinity, and hydrogel homogeneity.

When light encounters a material, it can interact with it in several different ways. These interactions depend on the nature of the light (its wavelength, frequency, energy, etc.) and the nature of the material. Light waves interact with an object by some combination of reflection, and transmittance with refraction. As such, an optically transparent material allows much of the light that falls on it to be transmitted, with little light being reflected. Materials which do not allow the transmission of light are called optically opaque or simply opaque.

In an embodiment, a silk fibroin hydrogel is optically transparent. In aspects of this embodiment, a silk fibroin hydrogel transmits, e.g., between about 75% to about 100% of the light. In some preferred aspects of this embodiment, a silk fibroin hydrogel transmits, e.g., between about 80% to about 90% of the light. In the most preferred aspects of this embodiment, a silk fibroin hydrogel transmits, e.g., between about 85% to about 90% of the light.

In another embodiment, a silk fibroin hydrogel is optically opaque. In aspects of this embodiment, a silk fibroin hydrogel transmits, e.g., between about 5% to about 75% of the light. In some preferred aspects of this embodiment, a silk fibroin hydrogel transmits, e.g., between about 10% to about 70% of the light. In the most preferred aspects of this embodiment, a silk fibroin hydrogel transmits, e.g., between about 15% to about 65% of the light.

In an embodiment, a silk fibroin hydrogel is optically translucent. In aspects of this embodiment, a silk fibroin hydrogel diffusely transmits, e.g., between about 75% to about 100% of the light. In some preferred aspects of this embodiment, a silk fibroin hydrogel diffusely transmits, e.g., between about 80% to about 95% of the light. In some the most preferred aspects of this embodiment, a silk fibroin hydrogel diffusely transmits, e.g., between about 85% to about 95% of the light.

After formation of a hydrogel described herein, the hydrogel can further processed. For example, to remove enhancer species and become a more complete, the formed hydrogel may be leeched against a solvent, such as, e.g., water, under ambient temperature and pressure conditions for three days with five changes of water. The hydrogel may be leeched against ultra-pure water of a volume at least 100-times that of the gel. More specifically, for example, the gels may be placed in a bulk of purified water and the rinse changed at hours 12, 24 and 48 with 15 mL gel per 1.5 L water. The number of rinses and volume ratios involved may be altered so long as the resultant hydrogel is substantially free of residual gelation enhancer.

A composition disclosed herein may be formulated using material processing constraints such as silk concentration and saline concentration to tailor material longevity in vivo. In one example, a silk hydrogel might be tailored for a persistence of five weeks to six weeks in vivo by using a 1%-3% (w/v) silk gel with 25%-50% (v/v) saline carrier. In another example, a silk hydrogel might be tailored for a persistence of two months to three months in vivo by using a 3%-5% (w/v) silk gel with 20%-40% (v/v) saline. In another example, a silk hydrogel might be tailored for a persistence of 5-6 months by using 4-6% (w/v) silk gel with 20-40% (v/v) saline. In another example, a silk hydrogel might be tailored for a persistence of 7-10 months by using a 6-8% (w/v) silk gel with 20-30% (v/v) saline. The persistence of these materials might also be increased or decreased by increasing or decreasing particle size respectively.

Gel emulsion saline content and gel silk concentration could be used to modify the mechanical profile of the silk gel materials for particular applications. For example, a gel emulsion of about 1% (w/v) to about 5% (w/v) silk gel concentration with 5%-95% lubricant (e.g., 5%-95% (w/v) saline/PBS) may be useful as a dermal filler, bulking agent, camouflage agent, intramuscular or sub-Q filler, or pharmaceutical delivery vector. A gel emulsion of, for example, about 5% (w/v) to about 8% (w/v) silk gel concentration with 0% to about 30% lubricant fluid may be useful in bone defects or cartilage defects.

Aspects of the present specification provide, in part, a composition comprising a gel phase including a hydrogel comprising a matrix polymer. The compositions disclosed herein can further comprise a hydrogel comprising one or more matrix polymers in addition to hydrogel particles comprising silk fibroin, or a hydrogel comprising one or more matrix polymers and silk fibroin. As used herein, the term "matrix polymer" refers to a polymer that can become part of and/or function as an extracellular matrix polymer and pharmaceutically acceptable salts thereof. Non-limiting examples of a matrix polymer include a glycosaminoglycan like chondroitin sulfate, dermatan sulfate, keratan sulfate, hyaluronan; a lubricin; a polysaccharide, and an elastic protein (like silk protein, resilin, resilin-like polypeptides (RLPs), elastin (including tropoelastin, fibrillin and fibullin), elastin-like polypeptides (ELPs), gluten (including gliadin and glutenin), abductin, byssus, and collagen). Non-limiting examples of a pharmaceutically acceptable salt of a matrix polymer includes sodium salts, potassium salts, magnesium salts, calcium salts, and combinations thereof. Matrix polymers useful in the compositions and methods disclosed herein are described in, e.g., Piron and Tholin, Polysaccharide Crosslinking, Hydrogel Preparation, Resulting Polysaccharides(s) and Hydrogel(s), uses Thereof, U.S. Patent Publication 2003/0148995; Lebreton, Cross-Linking of Low and High Molecular Weight Polysaccharides Preparation of Injectable Monophase Hydrogels; Lebreton, Viscoelastic Solutions Containing Sodium Hyaluronate and Hydroxypropyl Methyl Cellulose, Preparation and Uses, U.S. Patent Publication 2008/0089918; Lebreton, Hyaluronic Acid-Based Gels Including Lidocaine, U.S. Patent Publication 2010/0028438; and Polysaccharides and Hydrogels thus Obtained, U.S. Patent Publication 2006/0194758; and Di Napoli, Composition and Method for Intradermal Soft Tissue Augmentation, International Patent Publication WO 2004/073759, each of which is hereby incorporated by reference in its entirety.

Aspects of the present specification provide, in part, a composition comprising a hyaluronan. As used herein, the term "hyaluronic acid" is synonymous with "HA", "hyaluronic acid", and "hyaluronate" refers to an anionic, non-sulfated glycosaminoglycan polymer comprising disaccharide units, which themselves include D-glucuronic acid and D-N-acetylglucosamine monomers, linked together via alternating β-1,4 and β-1,3 glycosidic bonds and pharmaceutically acceptable salts thereof. Hyaluronan can be purified from animal and non-animal sources. Polymers of hyaluronan can range in size from about 5,000 Da to about 20,000,000 Da. Any hyaluronan is useful in the compositions disclosed herein with the proviso that the hyaluronan improves a condition of the skin, such as, e.g., hydration or elasticity. Non-limiting examples of pharmaceutically acceptable salts of hyaluronan include sodium hyaluronan, potassium hyaluronan, magnesium hyaluronan, calcium hyaluronan, and combinations thereof.

Aspects of the present specification provide, in part, a composition comprising a crosslinked matrix polymer. As used herein, the term "crosslinked" refers to the intermolecular bonds joining the individual polymer molecules, or monomer chains, into a more stable structure like a gel. As such, a crosslinked matrix polymer has at least one intermolecular bond joining at least one individual polymer molecule to another one. Matrix polymers disclosed herein may be crosslinked using dialdehydes and disufides crosslinking agents including, without limitation, multifunctional PEG-based cross linking agents, divinyl sulfones, diglycidyl ethers, and bis-epoxides. Non-limiting examples of hyaluronan crosslinking agents include divinyl sulfone (DVS), 1,4-butanediol diglycidyl ether (BDDE), 1,2-bis(2,3-epoxypropoxy)ethylene (EGDGE), 1,2,7,8-diepoxyoctane (DEO), biscarbodiimide (BCDI), pentaerythritol tetraglycidyl ether (PETGE), adipic dihydrazide (ADH), bis(sulfosuccinimidyl)suberate (BS), hexamethylenediamine (NMDA), 1-(2, 3-epoxypropyl)-2,3-epoxycyclohexane, or combinations thereof.

Aspects of the present specification provide, in part, a composition comprising a crosslinked matrix polymer having a degree of crosslinking. As used herein, the term "degree of crosslinking" refers to the percentage of matrix polymer monomeric units that are bound to a cross-linking agent, such as, e.g., the disaccharide monomer units of hyaluronan. Thus, a composition that that has a crosslinked matrix polymer with a 4% degree of crosslinking means that on average there are four crosslinking molecules for every 100 monomeric units. Every other parameter being equal, the greater the degree of crosslinking, the harder the gel becomes. Non-limiting examples of a degree of crosslinking include about 1% to about 15%.

In an embodiment, a composition comprises an uncrosslinked hyaluronan where the uncrosslinked hyaluronan comprises a combination of both high molecular weight hyaluronan and low molecular weight hyaluronan in a ratio of about 20:1, about 15:1, about 10:1, about 5:1, about 1:1, about 1:5 about 1:10, about 1:15, or about 1:20.

In another embodiment, a composition comprises an uncrosslinked hyaluronan where the uncrosslinked hyaluronan comprises a combination of both high molecular weight hyaluronan and low molecular weight hyaluronan, in various ratios. As used herein, the term "high molecular weight hyaluronan" refers to a hyaluronan polymer that has a molecular weight of 1,000,000 Da or greater. Non-limiting examples of a high molecular weight hyaluronan include a hyaluronan of about 1,500,000 Da, a hyaluronan of about 2,000,000 Da, a hyaluronan of about 2,500,000 Da, a hyaluronan of about 3,000,000 Da, a hyaluronan of about 3,500,000 Da, a hyaluronan of about 4,000,000 Da, a hyaluronan of about 4,500,000 Da, and a hyaluronan of about 5,000,000 Da. As used herein, the term "low molecular weight hyaluronan" refers to a hyaluronan polymer that has a molecular weight of less than 1,000,000 Da. Non-limiting examples of a low molecular weight hyaluronan include a hyaluronan of about 200,000 Da, a hyaluronan of about 300,000 Da, a hyaluronan of about 400,000 Da, a hyaluronan of about 500,000 Da, a hyaluronan of about 600,000 Da, a hyaluronan of about 700,000 Da, a hyaluronan of about 800,000 Da, and a hyaluronan of about 900,000 Da.

In other aspects of this embodiment, a composition comprises a crosslinked hyaluronan where the crosslinked hyaluronan has a mean molecular weight of, e.g., about 1,000,000 Da, about 1,500,000 Da, about 2,000,000 Da, about 2,500,000 Da, about 3,000,000 Da, about 3,500,000 Da, about 4,000,000 Da, about 4,500,000 Da, or about 5,000,000 Da. In yet other aspects of this embodiment, a composition comprises a crosslinked hyaluronan where the crosslinked hyaluronan has a mean molecular weight of, e.g., at least 1,000,000 Da, at least 1,500,000 Da, at least 2,000,000 Da, at least 2,500,000 Da, at least 3,000,000 Da, at least 3,500,000 Da, at least 4,000,000 Da, at least 4,500,000 Da, or at least 5,000,000 Da. In still other aspects of this embodiment, a composition comprises a crosslinked hyaluronan where the crosslinked hyaluronan has a mean molecular weight of, e.g., about 1,000,000 Da to about 5,000,000 Da, about 1,500,000 Da to about 5,000,000 Da, about 2,000,000 Da to about 5,000,000 Da, about 2,500,000 Da to about 5,000,000 Da, about 2,000,000 Da to about 3,000,000 Da, about 2,500,000 Da to about 3,500,000 Da, or about 2,000,000 Da to about 4,000,000 Da.

In other aspects of this embodiment, a composition comprises an uncrosslinked hyaluronan where the uncrosslinked hyaluronan has a mean molecular weight of, e.g., about 1,000,000 Da, about 1,500,000 Da, about 2,000,000 Da, about 2,500,000 Da, about 3,000,000 Da, about 3,500,000 Da, about 4,000,000 Da, about 4,500,000 Da, or about 5,000,000 Da. In yet other aspects of this embodiment, a composition comprises an uncrosslinked hyaluronan where the uncrosslinked hyaluronan has a mean molecular weight of, e.g., at least 1,000,000 Da, at least 1,500,000 Da, at least 2,000,000 Da, at least 2,500,000 Da, at least 3,000,000 Da, at least 3,500,000 Da, at least 4,000,000 Da, at least 4,500,000 Da, or at least 5,000,000 Da. In still other aspects of this embodiment, a composition comprises an uncrosslinked hyaluronan where the uncrosslinked hyaluronan has a mean molecular weight of, e.g., about 1,000,000 Da to about 5,000,000 Da, about 1,500,000 Da to about 5,000,000 Da, about 2,000,000 Da to about 5,000,000 Da, about 2,500,000 Da to about 5,000,000 Da, about 2,000,000 Da to about 3,000,000 Da, about 2,500,000 Da to about 3,500,000 Da, or about 2,000,000 Da to about 4,000,000 Da. In further aspects, a composition comprises an uncrosslinked hyaluronan where the uncrosslinked hyaluronan has a mean molecular weight of, e.g., greater than 2,000,000 Da and less than about 3,000,000 Da, greater than 2,000,000 Da and less than about 3,500,000 Da, greater than 2,000,000 Da and less than about 4,000,000 Da, greater than 2,000,000 Da and less than about 4,500,000 Da, greater than 2,000,000 Da and less than about 5,000,000 Da.

A composition disclosed herein comprises a gel phase including a silk fibroin hydrogel component or particle and matrix polymer hydrogel component or particle. In aspects of this embodiment, the percent amount of silk fibroin hydrogel present in a composition relative to matrix polymer hydrogel is from about 0.1% (v/v) to about 25% (v/v). In aspects of this embodiment, the percent amount of matrix polymer hydrogel present in a composition relative to silk fibroin hydrogel is from about 99.9% (v/v) to about 75% (v/v). In aspects of this embodiment, the ratio of silk fibroin hydrogel to matrix polymer hydrogel in the gel phase of a composition comprises, e.g., about 0.1% (v/v) silk fibroin hydrogel and about 99.9% (v/v) matrix polymer hydrogel, about 1% (v/v) silk fibroin hydrogel and about 99% (v/v) matrix polymer hydrogel, about 5% (v/v) silk fibroin hydrogel and about 95% (v/v) matrix polymer hydrogel, about 10% (v/v) silk fibroin hydrogel and about 90% (v/v) matrix polymer hydrogel, about 15% (v/v) silk fibroin hydrogel and about 85% (v/v) matrix polymer hydrogel, about 20% (v/v) silk fibroin hydrogel and about 80% (v/v) matrix polymer hydrogel, or about 25% (v/v) silk fibroin hydrogel and about 75% (v/v) matrix polymer hydrogel.

A composition disclosed herein may comprise a gel phase where the silk fibroin hydrogel component and matrix polymer hydrogel component are processed separately. The resulting processed hydrogel materials, e.g., hydrogel particles of both types, are then mixed together, such as, e.g., after a milling step and/or after re-homogenization in a carrier phase, to form the final composition. In addition, a matrix polymer may be initially mixed with depolymerized silk fibroin solution, with subsequent polymerization occurring only after the completion of the mixing step to form an integrated matrix polymer/silk fibroin composite hydrogel. Similarly, the silk fibroin and matrix polymers may be linked together to form a hydrogel composite that is then subsequently processed into the gel phase of the composition. Such linkage can occur by a typical cross linking method or by linking the matrix polymer to the silk fibroin hydrogel via a peptide linker disclosed herein, such as, e.g., a five-amino acid peptide "tail" and synthetic molecule. As disclosed herein, a composition may comprise a gel phase that comprises both separately processed hydrogel components as well as particles of hydrogel composites.

As a non-limiting example, a solution comprising about 1% to about 30% depolymerized silk fibroin may be mixed with about 6 mg/g to about 30 mg/g of hyaluronan having a degree of cross linking of from 0 to about 17% where the percent weight of the silk fibroin component is from about 1% to about 75%. As another non-limiting example, hydrogel particles comprising from about 1% to about 8% silk fibroin are mixed with hydrogel particles comprising about 6mg/g to about 30 mg/g of hyaluronan having a degree of cross linking of from 0 to about 17% where the percent weight of the silk fibroin component is from about 1% to about 75%. As yet another non-limiting example, a hydrogel composition comprising hydrogel particles comprising from about 1% to about 8% silk fibroin mixed together with a carrier phase (about 20% (v/v) to about 50% (v/v)) is mixed with a hydrogel composition comprising hydrogel particles comprising about 6 mg/g to about 30 mg/g of hyaluronan having a degree of cross linking of from 0 to about 17% where the percent weight of the silk fibroin component is from about 1% to about 75%.

Aspects of the present specification provide, in part, a composition comprising a silk fibroin hydrogel component or particle and matrix polymer hydrogel component or particle having an opacity. Opacity is the measure of impenetrability to electromagnetic or other kinds of radiation, especially visible light. An opaque object is neither transparent (allowing all light to pass through) nor translucent (allowing some light to pass through). In certain applications, it would be an advantage to have an opaque composition. For example, in applications where a composition disclosed herein is administered to a superficial region, an opaque composition provides coloration and appearance of the overlying skin.

In an embodiment, a composition comprising a silk fibroin hydrogel and a polymer matrix is optically opaque. In aspects of this embodiment, a composition comprising a silk fibroin hydrogel and a polymer matrix transmits, e.g., about 5% of the light to about 70% of the light. In some preferred aspects of this embodiment, a composition comprising a silk fibroin hydrogel and a polymer matrix transmits, e.g., about 10% of the light to about 65% of the light. In the most preferred aspects of this embodiment, a composition comprising a silk fibroin hydrogel and a polymer matrix transmits, e.g., about 15% of the light to about 60% of the light.

In aspects of this embodiment, a composition comprising a silk fibroin hydrogel and a polymer matrix exhibits, e.g., about 5% to about 100% reduction in tyndalling. In some preferred aspects of this embodiment, a composition comprising a silk fibroin hydrogel and a polymer matrix exhibits, e.g., about 10% to about 95% reduction in tyndalling. In the most preferred aspects of this embodiment, a composition comprising a silk fibroin hydrogel and a polymer matrix exhibits, e.g., about 15% to about 90% reduction in tyndalling.

Aspects of the present specification provide, in part, a composition disclosed herein exhibiting a dynamic viscosity. Viscosity is resistance of a fluid to shear or flow caused by either shear stress or tensile stress. Viscosity describes a fluid's internal resistance to flow caused by intermolecular friction exerted when layers of fluids attempt to slide by one another and may be thought of as a measure of fluid friction. The less viscous the fluid, the greater its ease of movement (fluidity).

Viscosity can be defined in two ways; dynamic viscosity (p, although n is sometimes used) or kinematic viscosity (v). Dynamic viscosity, also known as absolute or complex viscosity, is the tangential force per unit area required to move one horizontal plane with respect to the other at unit velocity when maintained a unit distance apart by the fluid. The SI physical unit of dynamic viscosity is the Pascal-second (Pa·s), which is identical to N·m−2·s. Dynamic viscosity can be expressed as $\tau = \mu dvx/dz$, where $\tau$=shearing stress, $\mu$=dynamic viscosity, and $dvx/dz$ is the velocity gradient over time. For example, if a fluid with a viscosity of one Pas is placed between two plates, and one plate is pushed sideways with a shear stress of one Pascal, it moves a distance equal to the thickness of the layer between the plates in one second. Dynamic viscosity symbolize by is also used, is measured with various types of rheometers, devices used to measure the way in which a liquid, suspension or slurry flows in response to applied forces.

Kinematic viscosity (v) is the ratio of dynamic viscosity to density, a quantity in which no force is involved and is defined as follows: $v = \mu/\rho$, where $\mu$ is the dynamic viscosity $\rho$ is density with the SI unit of $kg/m^3$. Kinematic viscosity is usually measured by a glass capillary viscometer as has an SI unit of $m^2/s$.

The viscosity of a fluid is highly temperature dependent and for either dynamic or kinematic viscosity to be meaningful, the reference temperature must be quoted. For the viscosity values disclosed herein, a dynamic viscosity is measured at 1 Pa with a cone/plane geometry 2°/40 cm and a temperature of 20° C. Examples of the dynamic viscosity of various fluids at 20° C. is as follows: water is about $1.0 \times 10^{-3}$ Pa·s, blood is about $3\text{-}4 \times 10^{-3}$ Pa·s, vegetable oil is about $60\text{-}85 \times 10^{-3}$ Pa·s, motor oil SE 30 is about 0.2 Pa·s, glycerin is about 1.4 Pa·s, maple syrup is about 2-3 Pa·s, honey is about 10 Pa·s, chocolate syrup is about 10-25 Pa·s, peanut butter is about 150-250 Pa·s, lard is about 1,000 Pa·s, vegetable shortening is about 1,200 Pa·s, and tar is about 30,000 Pa·s.

In aspects of this embodiment, a composition disclosed herein exhibits a dynamic viscosity of, e.g., about 10 Pa·s to about 1,200 Pa·s. In some preferred aspects of this embodiment, a composition disclosed herein exhibits a dynamic viscosity of, e.g., about 20 Pa·s to about 1,100 Pa·s. In the most preferred aspects of this embodiment, a composition disclosed herein exhibits a dynamic viscosity of, e.g., about 30 Pa·s to about 1,000 Pa·s.

Aspects of the present specification provide, in part, a composition disclosed herein is injectable. As used herein, the term "injectable" refers to a material having the properties necessary to administer the composition into a skin region of an individual using an injection device with a fine needle. As used herein, the term "fine needle" refers to a needle that is 27 gauge or smaller. Injectability of a composition disclosed herein can be accomplished by sizing the hydrogel particles as discussed above.

In aspect of this embodiment, a composition disclosed herein is injectable through a fine needle. In other aspects of this embodiment, a composition disclosed herein is injectable through a needle of, e.g., about 27 gauge, about 30 gauge, or about 32 gauge. In yet other aspects of this embodiment, a composition disclosed herein is injectable through a needle of, e.g., 27 gauge or smaller, 30 gauge or smaller, or 32 gauge or smaller. In still other aspects of this embodiment, a composition disclosed herein is injectable through a needle of, e.g., about 27 gauge to about 32 gauge.

In aspects of this embodiment, a composition disclosed herein can be injected with an extrusion force of about 60 N to about 5 N or less. In some preferred aspects of this embodiment, a composition disclosed herein can be injected with an extrusion force of about 55 N to about 10 N or less. In the most preferred aspects of this embodiment, a composition disclosed herein can be injected with an extrusion force of about 50 N to about 15 N or less.

Aspects of the present specification provide, in part, a composition disclosed herein exhibits cohesiveness. Cohesion or cohesive attraction, cohesive force, or compression force is a physical property of a material, caused by the intermolecular attraction between like-molecules within the material that acts to unite the molecules. A composition should be sufficiently cohesive as to remain localized to a site of administration. Additionally, in certain applications, a sufficient cohesiveness is important for a composition to retain its shape, and thus functionality, in the event of mechanical load cycling. As such, in one embodiment, a composition exhibits strong cohesive attraction, on par with water. In another embodiment, a composition exhibits low cohesive attraction. In yet another embodiment, a composition exhibits sufficient cohesive attraction to remain localized to a site of administration. In still another embodiment, a composition exhibits sufficient cohesive attraction to retain its shape. In a further embodiment, a composition exhibits sufficient cohesive attraction to retain its shape and functionality.

In aspects of this embodiment, a composition disclosed herein has a compression force of about 10 grams-force to about 3000 grams-force. In some preferred aspects of this embodiment, a composition disclosed herein has a compression force of about 20 grams-force to about 2000 grams-force. In the most preferred of this embodiment, a composition disclosed herein has a compression force of about 30 grams-force to about 1000 grams-force.

Aspects of the present specification provide, in part, a method of treating a soft tissue condition of an individual by administering a composition disclosed herein. As used herein, the term "treating," refers to reducing or eliminating in an individual a cosmetic or clinical symptom of a soft tissue condition characterized by a soft tissue imperfection, defect, disease, and/or disorder; or delaying or preventing in an individual the onset of a cosmetic or clinical symptom of a condition characterized by a soft tissue imperfection, defect, disease, and/or disorder. For example, the term "treating" can mean reducing a symptom of a condition characterized by a soft tissue defect, disease, and/or disorder by, e.g., at least 20%, at least 30%, at least 40%, at least 50%, at least 60%, at least 70%, at least 80%, at least 90% or at least 100%. The effectiveness of a compound disclosed herein in treating a condition characterized by a soft tissue defect, disease, and/or disorder can be determined by observing one or more cosmetic, clinical symptoms, and/or physiological indicators associated with the condition. An improvement in a soft tissue defect, disease, and/or disorder also can be indicated by a reduced need for a concurrent therapy. Those of skill in the art will know the appropriate symptoms or indicators associated with specific soft tissue defect, disease, and/or disorder and will know how to determine if an individual is a candidate for treatment with a compound or composition disclosed herein.

A composition or compound is administered to an individual. An individual is typically a human being. Typically, any individual who is a candidate for a conventional procedure to treat a soft tissue condition is a candidate for a method disclosed herein. In addition, the presently disclosed compositions and methods may apply to individuals seeking a small/moderate enlargement, shape change or contour alteration of a body part or region, which may not be technically possible or aesthetically acceptable with existing soft tissue implant technology. Pre-operative evaluation typically includes routine history and physical examination in addition to thorough informed consent disclosing all relevant risks and benefits of the procedure.

The composition and methods disclosed herein are useful in treating a soft tissue condition. A soft tissue condition includes, without limitation, a soft tissue imperfection, defect, disease, and/or disorder. Non-limiting examples of a soft tissue condition include breast imperfection, defect, disease and/or disorder, such as, e.g., a breast augmentation, a breast reconstruction, mastopexy, micromastia, thoracic hypoplasia, Poland's syndrome, defects due to implant complications like capsular contraction and/or rupture; a facial imperfection, defect, disease or disorder, such as, e.g., a facial augmentation, a facial reconstruction, Parry-Romberg syndrome, lupus erythematosus profundus, dermal divots, sunken checks, thin lips, nasal imperfections or defects, retro-orbital imperfections or defects, a facial fold, line and/or wrinkle like a glabellar line, a nasolabial line, a perioral line, and/or a marionette line, and/or other contour deformities or imperfections of the face; a neck imperfection, defect, disease or disorder; a skin imperfection, defect, disease and/or disorder; other soft tissue imperfections, defects, diseases and/or disorders, such as, e.g., an augmentation or a reconstruction of the upper arm, lower arm, hand, shoulder, back, torso including abdomen, buttocks, upper leg, lower leg including calves, foot including plantar fat pad, eye, genitals, or other body part, region or area, or a disease or disorder affecting these body parts, regions or areas; urinary incontinence, fecal incontinence, other forms of incontinence; and gastroesophageal reflux disease (GERD).

The amount of a composition used with any of the methods as disclosed herein will typically be determined based on the alteration and/or improvement desired, the reduction and/or elimination of a soft tissue condition symptom desired, the clinical and/or cosmetic effect desired by the individual and/or physician, and the body part or region being treated. The effectiveness of composition administration may be manifested by one or more of the following clinical and/or cosmetic measures: altered and/or improved soft tissue shape, altered and/or improved soft tissue size, altered and/or improved soft tissue contour, altered and/or improved tissue function, tissue ingrowth support and/or new collagen deposition, sustained engraftment of composition, improved patient satisfaction and/or quality of life, and decreased use of implantable foreign material.

For example, for breast augmentation procedures, effectiveness of the compositions and methods may be manifested by one or more of the following clinical and/or cosmetic measures: increased breast size, altered breast shape, altered breast contour, sustained engraftment, reduction in the risk of capsular contraction, decreased rate of liponecrotic cyst formation, improved patient satisfaction and/or quality of life, and decreased use of breast implant.

As another example, effectiveness of the compositions and methods in treating a facial soft tissue may be manifested by one or more of the following clinical and/or cosmetic measures: increased size, shape, and/or contour of facial feature like increased size, shape, and/or contour of lip, cheek or eye region; altered size, shape, and/or contour of facial feature like altered size, shape, and/or contour of lip, cheek or eye region shape; reduction or elimination of a wrinkle, fold or line in the skin; resistance to a wrinkle, fold or line in the skin; rehydration of the skin; increased elasticity to the skin; reduction or elimination of skin roughness; increased and/or improved skin tautness; reduction or elimination of stretch lines or marks; increased and/or improved skin tone, shine, brightness and/or radiance; increased and/or improved skin color, reduction or elimination of skin paleness; sustained engraftment of composition; decreased side effects; improved patient satisfaction and/or quality of life.

The amount of a composition used with any of the methods disclosed herein will typically be a therapeutically effective amount. As used herein, the term "therapeutically effective amount" is synonymous with "effective amount", "therapeutically effective dose", and/or " effective dose" and refers to the amount of compound that will elicit the biological, cosmetic or clinical response being sought by the practitioner in an individual in need thereof. As a non-limiting example, an effective amount is an amount sufficient to achieve one or more of the clinical and/or cosmetic measures disclosed herein. The appropriate effective amount to be administered for a particular application of the disclosed methods can be determined by those skilled in the art, using the guidance provided herein. For example, an effective amount can be extrapolated from in vitro and in vivo assays as described in the present specification. One skilled in the art will recognize that the condition of the individual can be monitored throughout the course of therapy and that the effective amount of a composition disclosed herein that is administered can be adjusted accordingly.

In aspects of this embodiment, the amount of a composition administered is, e.g., 0.01 g, 0.05 g, 0.1 g, 0.5 g, 1 g, 5 g, 10 g, 20 g, 30 g, 40 g, 50 g, 60 g, 70 g, 80 g, 90 g, 100 g, 150 g, or 200 g. In other aspects of this embodiment, the amount of a composition administered is, e.g., about 0.01 g to about 0.1 g, about 0.1 g to about 1 g, about 1 g to about 10 g, about 10 g to about 100 g, or about 50 g to about 200 g. In yet other aspects of this embodiment, the amount of a composition administered is, e.g., 0.01 mL, 0.05 mL, 0.1 mL, 0.5 mL, 1 mL, 5 mL, 10 mL, 20 mL, 30 mL, 40 mL, 50 mL, 60 mL, 70 g, 80 mL, 90 mL, 100 mL, 150 mL, or 200 mL. In other aspects of this embodiment, the amount of a composition administered is, e.g., about 0.01 mL to about 0.1 mL, about 0.1 mL to about 1 mL, about 1 mL to about 10 mL, about 10 mL to about 100 mL, or about 50 mL to about 200 mL.

Aspects of the present invention provide, in part, administering a composition disclosed herein. As used herein, the term "administering" means any delivery mechanism that provides a composition disclosed herein to an individual that potentially results in a clinically, therapeutically, or experimentally beneficial result. The actual delivery mechanism used to administer a composition to an individual can be determined by a person of ordinary skill in the art by taking into account factors, including, without limitation, the type of skin condition, the location of the skin condition, the cause of the skin condition, the severity of the skin condition, the degree of relief desired, the duration of relief desired, the particular composition used, the rate of excretion of the particular composition used, the pharmacodynamics of the particular composition used, the nature of the other compounds included in the particular composition used, the particular route of administration, the particular characteristics, history and risk factors of the individual, such as, e.g., age, weight, general health and the like, or any combination thereof. In an aspect of this embodiment, a composition disclosed herein is administered to a skin region of an individual by injection.

The route of administration of composition administered to an individual patient will typically be determined based on the cosmetic and/or clinical effect desired by the individual and/or physician and the body part or region being treated. A composition disclosed herein may be administered by any means known to persons of ordinary skill in the art including, without limitation, syringe with needle, catheter, topically, or by direct surgical implantation. The composition disclosed herein can be administered into a skin region such as, e.g., a dermal region or a hypodermal region. In addition, a composition disclosed herein can be administered once, or over a plurality of times. Ultimately, the timing used will follow quality care standards.

For a breast soft tissue replacement procedure, the route of administration may include axillary, periareolar, and/or inframammary routes. Alternatively or in addition, a composition may be delivered through a transaxillary endoscopic subpectoral approach. For a facial soft tissue replacement procedure, the route of administration can be frontal, temporal, zygomatic, periocular, amdibula, perioral or chin routes. In urinary incontinence procedures, the route of administration may include transurethral or periurethral routes. Alternatively or in addition, administration may be delivered via an antegrade route. The routes discussed herein do not exclude the use of multiple routes to achieve the desired clinical effect.

Aspects of the present invention provide, in part, a dermal region. As used herein, the term "dermal region" refers to the region of skin comprising the epidermal-dermal junction and the dermis including the superficial dermis (papillary region) and the deep dermis (reticular region). The skin is composed of three primary layers: the epidermis, which provides waterproofing and serves as a barrier to infection; the dermis, which serves as a location for the appendages of skin; and the hypodermis (subcutaneous adipose layer). The epidermis contains no blood vessels, and is nourished by diffusion from the dermis. The main type of cells which make up the epidermis are keratinocytes, melanocytes, Langerhans cells and Merkels cells.

The dermis is the layer of skin beneath the epidermis that consists of connective tissue and cushions the body from stress and strain. The dermis is tightly connected to the epidermis by a basement membrane. It also harbors many Mechanoreceptor/nerve endings that provide the sense of touch and heat. It contains the hair follicles, sweat glands, sebaceous glands, apocrine glands, lymphatic vessels and blood vessels. The blood vessels in the dermis provide nourishment and waste removal from its own cells as well as from the Stratum basale of the epidermis. The dermis is structurally divided into two areas: a superficial area adjacent to the epidermis, called the papillary region, and a deep thicker area known as the reticular region.

The papillary region is composed of loose areolar connective tissue. It is named for its fingerlike projections called papillae that extend toward the epidermis. The papillae provide the dermis with a "bumpy" surface that interdigitates with the epidermis, strengthening the connection between the two layers of skin. The reticular region lies deep in the papillary region and is usually much thicker. It is composed of dense irregular connective tissue, and receives its name from the dense concentration of collagenous, elastic, and reticular fibers that weave throughout it. These protein fibers give the dermis its properties of strength, extensibility, and elasticity. Also located within the reticular region are the roots of the hair, sebaceous glands, sweat glands, receptors, nails, and blood vessels. Tattoo ink is held in the dermis. Stretch marks from pregnancy are also located in the dermis.

The hypodermis lies below the dermis. Its purpose is to attach the dermal region of the skin to underlying bone and muscle as well as supplying it with blood vessels and nerves. It consists of loose connective tissue and elastin. The main cell types are fibroblasts, macrophages and adipocytes (the hypodermis contains 50% of body fat). Fat serves as padding and insulation for the body.

In an aspect of this embodiment, a composition disclosed herein is administered to a skin region of an individual by injection into a dermal region or a hypodermal region. In aspects of this embodiment, a composition disclosed herein is administered to a dermal region of an individual by injection into, e.g., an epidermal-dermal junction region, a papillary region, a reticular region, or any combination thereof.

Aspects of the present specification disclose, in part, a method of treating a soft tissue condition of an individual, the method comprising the steps of administering a composition disclosed herein to a site of the soft tissue condition of the individual, wherein the administration of the composition improves the soft tissue condition, thereby treating the soft tissue condition. In aspects of this embodiment, a soft tissue condition is a breast tissue condition, a facial tissue condition, a neck condition, a skin condition, an upper arm condition, a lower arm condition, a hand condition, a shoulder condition, a back condition, a torso including abdominal condition, a buttock condition, an upper leg condition, a lower leg condition including calf condition, a foot condition including plantar fat pad condition, an eye condition, a genital condition, or a condition effecting another body part, region or area.

Other aspects of the present specification disclose, in part, a method of treating a skin condition comprises the step of administering to an individual suffering from a skin condition a composition disclosed herein, wherein the administration of the composition improves the skin condition, thereby treating the skin condition. In an aspect of this embodiment, a skin condition is a method of treating skin dehydration comprises the step of administering to an individual suffering from skin dehydration a composition disclosed herein, wherein the administration of the composition rehydrates the skin, thereby treating skin dehydration. In another aspect of this embodiment, a method of treating a lack of skin elasticity comprises the step of administering to an individual suffering from a lack of skin elasticity a composition disclosed herein, wherein the administration of the composition increases the elasticity of the skin, thereby treating a lack of skin elasticity. In yet another aspect of this embodiment, a method of treating skin roughness comprises the step of administering to an individual suffering from skin roughness a composition disclosed herein, wherein the administration of the composition decreases skin roughness, thereby treating skin roughness. In still another aspect of this embodiment, a method of treating a lack of skin tautness comprises the step of administering to an individual suffering from a lack of skin tautness a composition disclosed herein, wherein the administration of the composition makes the skin tauter, thereby treating a lack of skin tautness.

In a further aspect of this embodiment, a method of treating a skin stretch line or mark comprises the step of administering to an individual suffering from a skin stretch line or mark a composition disclosed herein, wherein the administration of the composition reduces or eliminates the skin stretch line or mark, thereby treating a skin stretch line or mark. In another aspect of this embodiment, a method of treating skin paleness comprises the step of administering to an individual suffering from skin paleness a composition disclosed herein, wherein the administration of the composition increases skin tone or radiance, thereby treating skin paleness. In another aspect of this embodiment, a method of treating skin wrinkles comprises the step of administering to an individual suffering from skin wrinkles a composition disclosed herein, wherein the administration of the composition reduces or eliminates skin wrinkles, thereby treating skin wrinkles. In yet another aspect of this embodiment, a method of treating skin wrinkles comprises the step of administering to an individual a composition disclosed herein, wherein the administration of the composition makes the skin resistant to skin wrinkles, thereby treating skin wrinkles.

Aspects of the present specification provide, in part, administration of a composition disclosed herein wherein such administration promotes new collagen deposition. The compositions comprising a silk fibroin hydrogel component or particle and matrix polymer hydrogel component or particle support tissue ingrowth and new deposition of collagen (Example 21).

In an embodiment, administration of a composition comprising a silk fibroin hydrogel component and a matrix polymer hydrogel component as disclosed herein increases new collagen deposition. In aspects of this embodiment, administration of a composition comprising a silk fibroin hydrogel component and a matrix polymer hydrogel component as disclosed herein increases new collagen deposition by about 10%, about 20%, about 30%, about 40%, about 50%, about 60%, about 70%, about 80%, about 90%, or about 100%, relative to a the same or similar composition comprising the matrix polymer hydrogel component, but lacking the silk fibroin hydrogel component. In other aspects of this embodiment, administration of a composition comprising a silk fibroin hydrogel component and a matrix polymer hydrogel component as disclosed herein increases new collagen deposition by at least 25%, at least 50%, at least 75%, at least 100%, at least 125%, at least 150%, at least 175%, at least 200%, at least 225%, at least 250%, at least 275%, or at least 300%, relative to a the same or similar composition comprising the matrix polymer hydrogel component, but lacking the silk fibroin hydrogel component. In yet other aspects of this embodiment, administration of a composition comprising a silk fibroin hydrogel component and a matrix polymer hydrogel component as disclosed herein increases new collagen deposition by about 10% to about 100%, about 50% to about 150%, about 100% to about 200%, about 150% to about 250%, about 200% to about 300%, about 350% to about 450%, about 400% to about 500%, about 550% to about 650%, about 600% to about 700%, relative to a the same or similar composition comprising the matrix polymer hydrogel component, but lacking the silk fibroin hydrogel component.

EXAMPLES

The following examples illustrate representative embodiments now contemplated, but should not be construed to limit the disclosed purified silk fibroin and method for purifying such silk fibroins, hydrogels comprising such silk fibroin with or without an amphiphilic peptide and methods for making hydrogels comprising such silk fibroin and the use of silk fibroin hydrogels in a variety of medical uses, including, without limitation fillers for tissue space, templates for tissue reconstruction or regeneration, scaffolds for cells in tissue engineering applications and for disease models, a surface coating to improve medical device function, or as a platform for drug delivery.

Example 1

Preparation of a Water-Soluble Silk Fibroin Solution

A 9.3 M LiBr solution was prepared by slowly dissolving 77.54 g of LiBr in 76.28 mL of MilliQ water. The LiBr solution was kept at 60° C. 24 g of sericin extracted knitted silkworm silk yarn was slowly submerged in the LiBr solution. The LiBr and silk solution was incubated in an oven at 60° C. for 6 hours. The solution was then loaded into a dialysis cassette MWCO 3.5 KDa and dialyzed against MilliQ water in a 4 L beaker at room temperature for 72 hours, changing the water at 1 hour, 4 hours, 12 hours and then twice a day.

Example 2

80% HA-20% Silk Fibroin Crosslinked Gel Made Sing EDC Chemistry and HMDA 1.2 mL of a 7 wt % Silk Fibroin (SF) MilliQ water solution and 20 mg of the diamine cross linker HMDA.2HCl was added to 13.8 mL of MilliQ water. 336 mg of high molecular weight hyaluronic acid (HA) was added to the solution. The mixture was allowed to hydrate for 60 minutes and homogenized by passing 30 times syringe-to-syringe. 576 mg of MES buffer was mixed with 321.6 mg of EDC and 72.9 mg of sulfoNHS in 5 mL MilliQ water. The reagent solution was mixed to the HA/SF solution by passing between syringes 30 times. The mixture was transferred to glass vials and left to react overnight at 4° C. The gel was sized using a 100 um mesh and centrifuged at 4000 rpm for 5 minutes. The sized gel was transferred to a cellulose ester membrane dialysis tubing MWCO 20 KDa and dialyzed against 1×PBS for 8 days at room temperature, changing the buffer twice a day. After dialysis, the gel was sized using a 60 um mesh, dispensed in 1 ml COC syringes, centrifuged at 5000 RPM for 5 min, and moist heat sterilized for 5 minutes at 128° C.

Example 3

80% HA-20% Silk Fibroin Gel Crosslinked Using EDC Chemistry and Lysine Methyl Ester 1.2 mL of a 7 wt % Silk Fibroin (SF) MilliQ water solution and 24.4 mg of lysine methyl ester was added to 13.8 mL of MilliQ water. 336 mg of high molecular weight hyaluronic acid (HA) was added to the solution. The mixture was allowed to hydrate for 60 minutes and homogenized by passing 30 times syringe-to-syringe. 576 mg of MES buffer were mixed with 321.6 mg of EDC and 72.9 mg of sulfoNHS in 5 mL MilliQ water. The reagent solution was mixed to the HA/SF solution by passing between syringes 30 times. The mixture was transferred to glass vials and left to react overnight at 4° C. The gel was sized using a 100 um mesh and centrifuged at 4000 rpm for 5 minutes. The sized gel was transferred to a cellulose ester membrane dialysis tubing MWCO 20 KDa and dialyzed against 1×PBS for 8 days at room temperature, changing the buffer twice a day. After dialysis, the gel was sized using a 60 um mesh, dispensed in 1 ml COC syringes, centrifuged at 5000 RPM for 5 min, and moist heat sterilized for 5 minutes at 128° C.

Example 4

80% HA-20% SF Gel Cross Linked Using BDDE 2.4 mL of a 7 wt % Silk Fibroin (SF) MilliQ water solution and 1.25 mL of 1N NaOH MilliQ water solution were added to 1.35 mL MilliQ water. 494 mg of HMW HA was added to the SF/NaOH solution and allowed to hydrate for 60 minutes and homogenized by passing 30 times syringe-to-syringe. 85 mg of BDDE was added to the mixture and passed between syringes 30 times. The mixture was cured in a water bath at 50° C. for 2 hours. The gel was neutralized by adding 135 pL of 37% HCl and 4.86 mL PBS and passed between syringes 30 times. 7.5 mL of PBS was added to the gel and the gel was allowed to swell overnight at 4° C. The final HA/SF concentration of the gel was about 5 wt %. The gel was sized using a 100 um mesh and centrifuged at 4000 rpm for 5 minutes. The sized gel was transferred to a cellulose ester membrane dialysis tubing MWCO 20 KDa and dialyzed against 1×PBS for 8 days at 4° C., changing the buffer twice a day. After dialysis, the gel was dispensed in 1 ml COC syringes, centrifuged at 5000 RPM for 5 min, and sterilized with moist steam for 5 minutes at 128° C.

Example 5

HA-SF Gel Rheology

An oscillatory parallel plate rheometer (Anton Paar Physica MCR 301) wais used to measure the rheological properties of the gels. A plate diameter of 25 mm was used at a gap height of 1 mm. Measurements were performed at a constant temperature of 25° C. Each measurement consisted of a frequency sweep from 1 to 10 Hz at a constant strain of 2% and a logarithmic increase of frequency followed by a strain sweep from 1 to 300% at a constant frequency of 5 Hz with a logarithmic increase in strain. The storage modulus (G') and the loss modulus (G") are obtained from the strain sweep at 1% strain.

TABLE 1

Storage and loss moduli of gels obtained in Examples 2 to 4

| Sample ID | Storage Modulus G' (Pa) | Loss Modulus G" (Pa) |
|---|---|---|
| Example 2 | 672 | 21 |
| Example 3 | 998 | 35 |
| Example 4 | 268 | 114 |

Example 6

HA-SF Gel Extrusion Force

The force required to extrude the gels through a 30 gauge needle was measured using an Instron 5564 and a Bluehill 2 software. The gels were extruded from a 1 ml COC syringe through a 30G½ TSK needle. The plunger was pushed at a speed of 100 mm/min for 11.35 mm, and the extrusion force was recorded.

TABLE 2

Extrusion force of gels obtained in Examples 2 and 3

| Sample ID | Extrusion Force (N) |
|---|---|
| Example 2 | 100 |
| Example 3 | 98 |

Example 7

Bacterial Endotoxin

The gels were tested for bacterial endotoxin content by performing a Limulus Amebocyte Lysate (LAL) test using a Charles River Endosafe®-PTS™ system. 4 droplets of 25 µL were loaded onto FDA-licensed cartridges with a sensitivity of 0.005 EU/mL and the cartridge was inserted in the Endosafe®-PTS™.

TABLE 3

Bacterial Endotoxin concentration of gels obtained in Examples 2 and 3

| Sample ID | Bacterial Endotoxin (EU/mL) |
|---|---|
| Example 2 | <5 |
| Example 3 | <5 |

Example 8

Use of Dermal Filler Composition for Treating a Facial Defect of the Cheek

This example illustrates the use of compositions and methods disclosed herein for treating a facial defect of the cheek. A 28-year-old woman presents with a lean face. She felt her face looked old, sad and bitter because of the less fullness of her check contour. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A composition comprising silk fibroin hydrogel component and a hyaluronan component is administered subcutaneously and under superficial musculoaponeurotix system into the checks regions; about 15 mL of composition into the left and right cheeks. The individual is monitored for approximately 7 days. The physician evaluates the cheeks tissue and determines that the treatment was successful. Both the woman and her physician are satisfied with the results of the procedure because she looked younger. Approximately one month after the procedure, the woman indicates that his quality of life has improved.

Example 9

Use of Dermal Filler Composition for Treating Wrinkles

This example illustrates the use of compositions and methods disclosed herein for treating wrinkles. A 55-year-old woman presents with wrinkles around the eyes and cheek areas. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A composition comprising silk fibroin hydrogel component and a hyaluronan component is administered subcutaneously and under superficial musculoaponeurotix system into the upper eyelid and cheek regions; about 1.5 mL of composition into the left and right eyelid and cheek regions. The individual is monitored for approximately 7 days. The physician evaluates the facial regions and determines that the treatment was successful. Both the woman and her physician are satisfied with the results of the procedure because she looked younger. Approximately one month after the procedure, the woman indicates that his quality of life has improved.

Example 10

Use of Dermal Filler Composition for Treating a Breast Defect

This example illustrates the use of compositions and methods disclosed herein for treating a breast defect. A 32-year-old woman presents with complaints that the medial portions of her breast implants are visible, which accentuated the "bony" appearance of her sternum. In addition she felt her breast are too far apart. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A composition comprising silk fibroin hydrogel component and a hyaluronan component is administered subcutaneously over the lateral sternum and medial breast bilaterally, 15 mL on the right and 10 mL on the left. The composition is administered in a tear like fashion to increase the surface area to volume ratio. The individual is monitored for approximately 7 days. The physician evaluates the breasts and determines that the treatment was successful. Both the woman and her physician are satisfied with the results of the procedure. Approximately one month after the procedure, the woman indicates that his quality of life has improved.

Example 11

Use of Dermal Filler Composition for Breast Augmentation

This example illustrates the use of compositions and methods disclosed herein for breast augmentation. A 28-year-old woman presents micromastia or breast hypoplasia. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A composition comprising silk fibroin hydrogel component and a hyaluronan component is administered subcutaneously using axillary, periareolar, and inframammary routes bilaterally, 90 mL on the right and 145 mL on the left. The composition is administered in a tear like fashion to increase the surface area to volume ratio. The individual is monitored for approximately 7 days. The physician evaluates the breasts and determines that the treatment was successful. Both the woman and her physician are satisfied with the results of the procedure. Approximately one month after the procedure, the woman indicates that his quality of life has improved.

Example 12

Adipose Tissue Transplant for Breast Disorder

This example illustrates the use of compositions and methods disclosed herein for treating a breast disorder. A 29-year-old woman presents with bilateral tiberous breast deformity. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A composition comprising silk fibroin hydrogel component and a hyaluronan component is administered subcutaneously in multiple planes axillary, periareolar, and inframammary routes bilaterally, 180 mL on the right and 170 mL on the left. The composition is administered in a tear like fashion to increase the surface area to volume ratio. The individual is monitored for approximately 7 days. The physician evaluates the breasts and determines that the treatment was successful. Both the woman and her physician are satisfied with the results of the procedure. Approximately one month after the procedure, the woman indicates that his quality of life has improved.

In closing, it is to be understood that although aspects of the present specification have been described with reference to the various embodiments, one skilled in the art will readily appreciate that the specific examples disclosed are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing quantities of ingredients, properties such as molecular weight, reaction conditions, and so forth used in the specification and claims are to be understood as being modified in all instances by the term "about." As used herein, the term "about" means that the item, parameter or term so qualified encompasses a range of plus or minus ten percent above and below the value of the stated item, parameter or term. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

We claim:

1. An injectable composition for treating a soft tissue condition, the composition comprising a gel comprising a silk crosslinked to a hyaluronic acid via amide bonding to a multiamine cross linker, wherein the multiamine cross linker is selected from the group consisting of (i) 3-[3-(3-amino propoxy)-2,2-bis(3-amino-propoxymethyl)-propoxy]propylamine (4AA) or (ii) a linear diamine cross linker selected from the group consisting of a hexamethylene diamine (HMDA), lysine, lysine methyl ester, and lysine ethyl ester.

2. The injectable composition of claim 1, wherein the silk is a sericin-depleted silk fibroin having about 0% w/w to about 4% w/w of a native amount of sericin.

3. The injectable composition of claim 1, wherein the composition comprises a saline carrier, and the gel is combined with the saline carrier in a formulation comprising one selected from the group consisting of about 1% to about 3% (w/v) gel with about 25% to about 50% (v/v) saline carrier; about 3% to about 5% (w/v) gel with about 20% to about 40% (v/v) saline; about 4% to about 6% (w/v) gel with about 20% to about 40% (v/v) saline; and about 6% to about 8% (w/v) gel with about 20% to about 30% (v/v) saline.

4. The injectable composition of claim 1, wherein the gel has a degree of crosslinking in the range of about 1% to about 15%.

5. The injectable composition of claim 1, wherein the hyaluronic acid is selected from the group consisting of sodium hyaluronan, potassium hyaluronan, magnesium hyaluronan, calcium hyaluronan, and combinations thereof.

6. The injectable composition of claim 1, wherein the hyaluronic acid comprises a combination of a high molecular weight hyaluronic acid and a low molecular weight hyaluronic acid in a ratio of the high molecular weight hyaluronic acid to the low molecular weight hyaluronic acid of about 20:1, about 15:1, about 10:1, about 5:1, about 1:1, about 1:5 about 1:10, about 1:15, or about 1:20;
wherein the high molecular weight hyaluronic acid has a molecular weight of 1,000,000 Da or greater and the low molecular weight hyaluronic acid has a molecular weight of less than 1,000,000 Da.

7. The injectable composition of claim 1, wherein the composition is configured to administer the gel to a subject in an amount in the range of about 0.01 g to about 200 g.

8. The injectable composition of claim 1, wherein the silk and the hyaluronic acid are present in a weight ratio of hyaluronic acid to silk in the range of about 10:1 to about 1:10.

9. The injectable composition of claim 1, wherein the silk and the hyaluronic acid are present in a weight ratio of hyaluronic acid to silk in the range of about 5:1 to about 2:1.

10. A method for treating a soft tissue condition in an individual in need thereof, the method comprising the step of administering the injectable composition of claim 1 into a skin region of the individual, wherein the administration improves the soft tissue condition.

11. A method for breast augmentation or breast reconstruction comprising the step of administering the injectable composition of claim 1 in a breast region, wherein the composition further comprises adipose cells or adipose-derived progenitor cells.

12. An injectable composition for treating a soft tissue condition, wherein the composition comprises a gel comprising a silk crosslinked to a hyaluronic acid via amide bonding to a multiamine cross linker selected from the group consisting of (i) 3-[3-(3- amino propoxy)-2,2-bis(3-amino-propoxymethyl)-propoxy]propylamine (4AA) or (ii) a linear diamine cross linker selected from the group consisting of a hexamethylene diamine (HMDA), lysine, lysine methyl ester, and lysine ethyl ester, wherein the composition is prepared by the process of:
i. reacting at least one -COOH group on a glucuronic acid residue of the hyaluronic acid with a carbodiimide coupling agent, whereby an activated hyaluronic acid is produced; and
ii. cross-linking the activated hyaluronic acid and the silk using a multiamine cross linker.

13. The composition of claim 12, further comprising prior to the step of cross-linking, functionalizing one or more tyrosine residues on the silk using a diazo chemical reaction to provide introduce a —COOH group onto the one or more tyrosine residues.

14. The composition of claim 12, further comprising after the step of cross-linking, sterilizing the gel in steam at 128° C. for at least 5 minutes.

15. The injectable composition of claim 12, wherein the silk and the hyaluronic acid are present in the gel in a weight ratio of hyaluronic acid to silk in the range of about 5:1 to about 2:1.

16. The injectable composition of claim 12, wherein the carbodiimide agent is 1-ethyl-3-[3-dimethylam inopropyl] carbodiim ide (EDC) and further comprising using a water-soluble coupling agent selected from N-hydroxysuccinimide (NHS) or a N-hydroxysulfosuccinimide (sulfoNHS) in conjunction with the carbodiimide coupling agent.

* * * * *